United States Patent [19]

Benesh et al.

[11] Patent Number: 5,088,504
[45] Date of Patent: Feb. 18, 1992

[54] MACHINE AND METHOD FOR MEASURING SKELETAL MISALIGNMENTS

[75] Inventors: Peter Benesh, Monroe; Ralph R. Gregory, deceased, late of Monroe, both of Mich., by Keith E. Denton, legal representative

[73] Assignee: National Upper Cervical Chiropractic Research Assn., Monroe, Mich.

[21] Appl. No.: 601,910

[22] Filed: Oct. 23, 1990

[51] Int. Cl.$^5$ ............................................. A61B 5/103
[52] U.S. Cl. ...................................... 128/781; 33/515
[58] Field of Search .................. 128/774, 781; 33/515; 177/25.13

[56] References Cited

U.S. PATENT DOCUMENTS

| | | | |
|---|---|---|---|
| 3,027,761 | 4/1962 | Lauro | 73/172 |
| 4,033,329 | 7/1977 | Gregory et al. | 128/2 S |
| 4,036,213 | 7/1977 | Gregory | 128/2 S |
| 4,221,213 | 9/1980 | Gregory et al. | 128/70 |
| 4,914,611 | 4/1990 | Yamanska et al. | 177/25.13 |

FOREIGN PATENT DOCUMENTS

| | | | |
|---|---|---|---|
| 0245098 | 11/1987 | European Pat. Off. | 128/781 |
| 0028619 | 2/1987 | Japan | 177/25.13 |
| 8001419 | 10/1981 | Netherlands | 128/774 |

Primary Examiner—Max Hindenburg
Attorney, Agent, or Firm—Harness, Dickey & Pierce

[57] ABSTRACT

The machine of the present invention measures and records in terms of the orientation planes of motion the presence of, the location, of and the severity of the postural distortion-stress effects of C-1 subluxations on the human body, making possible thereby statistical analyses between C-1 misalignments (determined by X-ray analysis) and such postural distortion-stress effects on the skeletal framework as directly result from the misalignment interferences of C-1 on the nervous system and its normal functioning. This machine can demonstrate the postural distortion-stress effects of C-1 subluxation on the spine by checking the malpositional relationships of upper thoracic vertebral segments and pelvis prior to and subsequent to C-1 correction, indicating thereby the corrections obtainable throughout the spine and thus reducing the need for repeated applications of X-radiation to the patient. The machine has movable elements which provide indications of corrections or displacement and has a pair of weight sensitive platforms with horizontally adjustable pads (foot guides). The platforms are coupled to force transducers which indicate a means for measuring the portion of total body weight that is supported by each of the patient's feet. The pads are individually or simultaneously adjustable toward and away from each other to properly space the feet relative to the ilii.

14 Claims, 3 Drawing Sheets

MACHINE AND METHOD FOR MEASURING SKELETAL MISALIGNMENTS

BACKGROUND OF THE INVENTION

The orthodox premise of chiropractic practice is defined as the correction, restoration toward normal, or replacement of misalignments of subluxated vertebrae by the act of adjusting such subluxated vertebrae to their normal, relative position. A subluxation is a condition caused by vertebrae misalignments. A subluxation results from the abnormal movement of subluxated vertebra, which through pressure, or interference of an irritation producing mechanism detrimentally affects the nervous system. In particular, this pressure affects the spinal cord, which is lodged in the vertebral canal, and can cause abnormal functioning of the central nervous system. This may manifest itself in a variety of conditions and/or diseases in humans.

The present invention is based on the premise that the atlas vertebra also known as "C-1", is the most important vertebra in the spinal column. This is because C-1 is the uppermost vertebra of the human spine, and thereby supports the skull in close proximity to the caudal region of the brain stem.

Observations in a large number of cases have shown that pelvic distortion is accompanied by, and correlates with, some misalignment in the C-1 vertebrae, in one or more planes of its positional relationship to the occiput. It is desirable to be able to quickly, accurately, and reproducibly, measure these misalignments.

It has long been known to chiropractors that it is important to correct occiputal-atlanto-axial subluxations. Typically, in the past, correction of such subluxations has been accomplished by using X-rays as the primary source of information as to the location of C-1, and subjacent vertebrae and as to the positional relationship of C-1 to the occiput. In the prior normal routine, a series of X-rays were taken in the three planes of motion in which spinal vertebrae can abnormally move and a listing was prepared from an analysis of the degrees of abnormal motion. After adjustment, a second series of X-rays was taken and an appraisal made of the degree of correction of the misalignments.

Improvements in the apparatus to measure postural distoration-stress effects (upper thoracic and pelvic distortions) by means other than X-ray as described in U.S. Pat. Nos. 4,036,213 and 4,033,329, provide accurate information as to the effects of an atlas adjustment or the need for further adjustment. As a result, the need for X-rays to check skeletal misalignments is reduced. Thus, it would be desirable to provide further improvements in apparatus and technique for correlating postural distortion-stress effects with X-ray determination of misalignments to minimize the use of X-rays.

SUMMARY OF THE INVENTION

The invention pertains to an improved method for providing a body of information with regard to skeletal misalignments of a patient. The invention provides a means for determining the lateral weight distribution in the patient while maintaining accurate and exact foot placement. As a result, the patent's weight distribution can then be related to the skeletal distortions.

A machine is provided which has a hollow base and a vertical column at one end. Forwardly of the column a pair of platforms are mounted for receiving the feet of the patient who stands thereon. The platforms are coupled to force transducers which are used to measure the portion of total body weight that is supported by each of the patient's feet. Each of the two platforms includes a means for accurately locating the patient's feet on the platform directly below the patient's ilii. A cylindrical sleeve is mounted on the column for up, down and angular movement thereon with the column having a weight therein connected to a cable which passes out at the top of the column over a counterbalancing wheel with the end of the cable connected to the transverse plane indicator which is secured to the top of the cylindrical sleeve. A transverse plate is mounted on the cylindrical sleeve in fixed relation thereto having a pelvic vernier bar pivoted thereto at its center. The bar carries a pair of laterally adjustable housings from which pivoted pelvic arms extend forwardly to engage the ilii of the patient, the spacing of which indicates the degree to which the feet of the patient should be spread apart. The pelvic arms may be adjusted from a forward position illustrated to a position 45 degrees and 90 degrees therefrom to be retained in either position by a lever which locks the arms after adjustment. A scale at each end of the fixed arm designates the position in the frontal plane of the pelvic vernier bar.

Each platform has locating means thereon in the nature of pads or plates having adjustable means thereon for moving the pads toward and away from each other to space the feet of a patient standing on the platforms in accordance to the reading of the spacing of the arms which engage the ilii. The machine also has a vertebral probe slide bar extending upwardly from the transverse plate fixed to the cylindrical sleeve which has a slideway therein for a vertical probe which may be moved to key vertebrae in the spinal column and checked for displacement of such key vertebra may be obtained on a scale on an upright portion on the fixed transverse plate. U.S. Pat. Nos. 4,033,329 and 4,036,213, owned by the Assignee of this application provides further details of the machine and process for determining vertebrae locations in humans.

BRIEF DESCRIPTION OF THE DRAWINGS

FIG. 5 is a partial sectional view of the structure illustrated in FIG. 3, taken on the line 5—5 thereof; and FIG. 6 is a partial sectional view of the structure illustrated in FIG. 3, taken on the line 6—6 thereof.

DESCRIPTION OF THE PREFERRED EMBODIMENT

Figure 1:
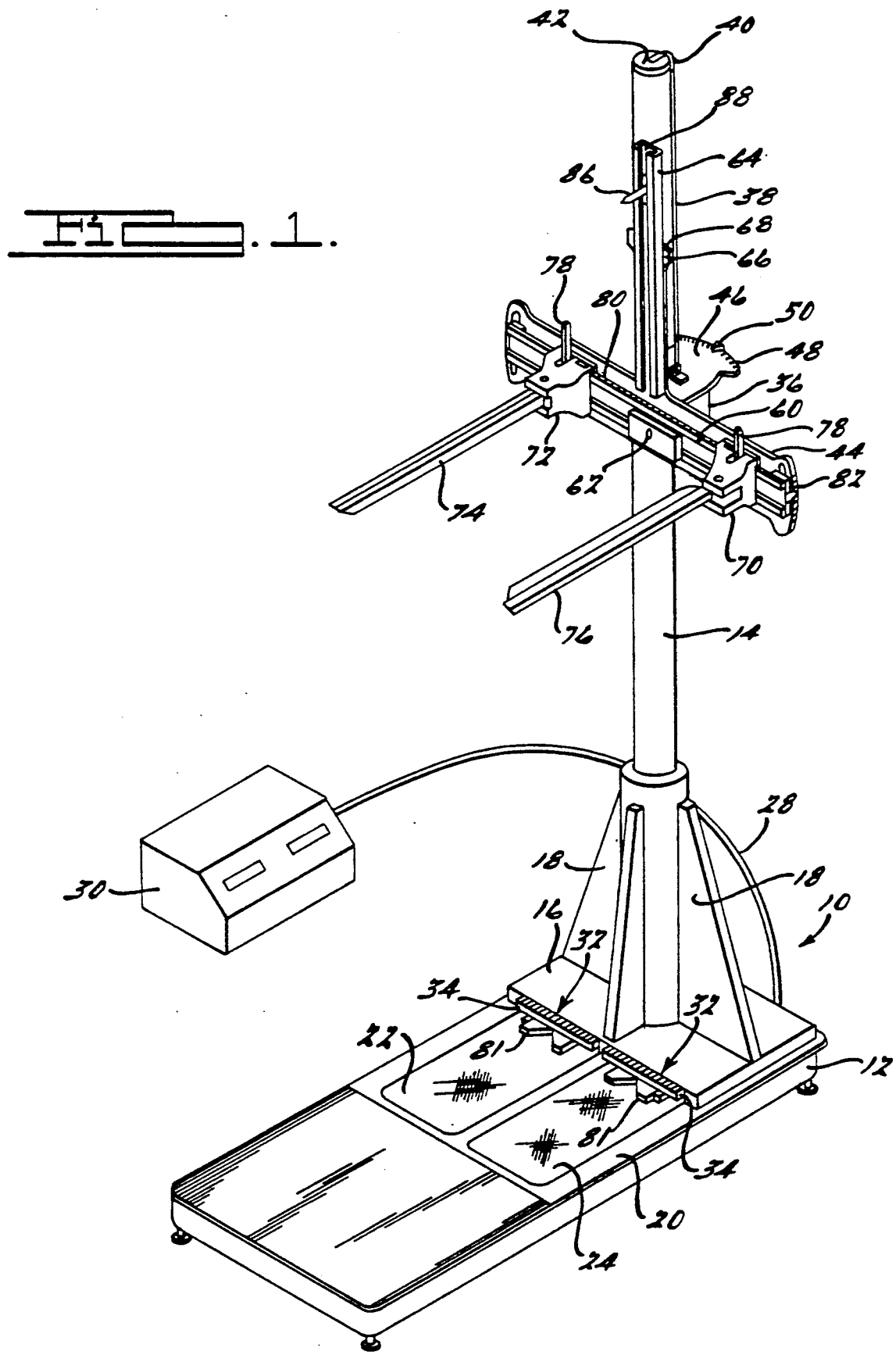
FIG. 1 is a perspective view of a skeleton checking machine embodying features of the present invention.
Figure 2:
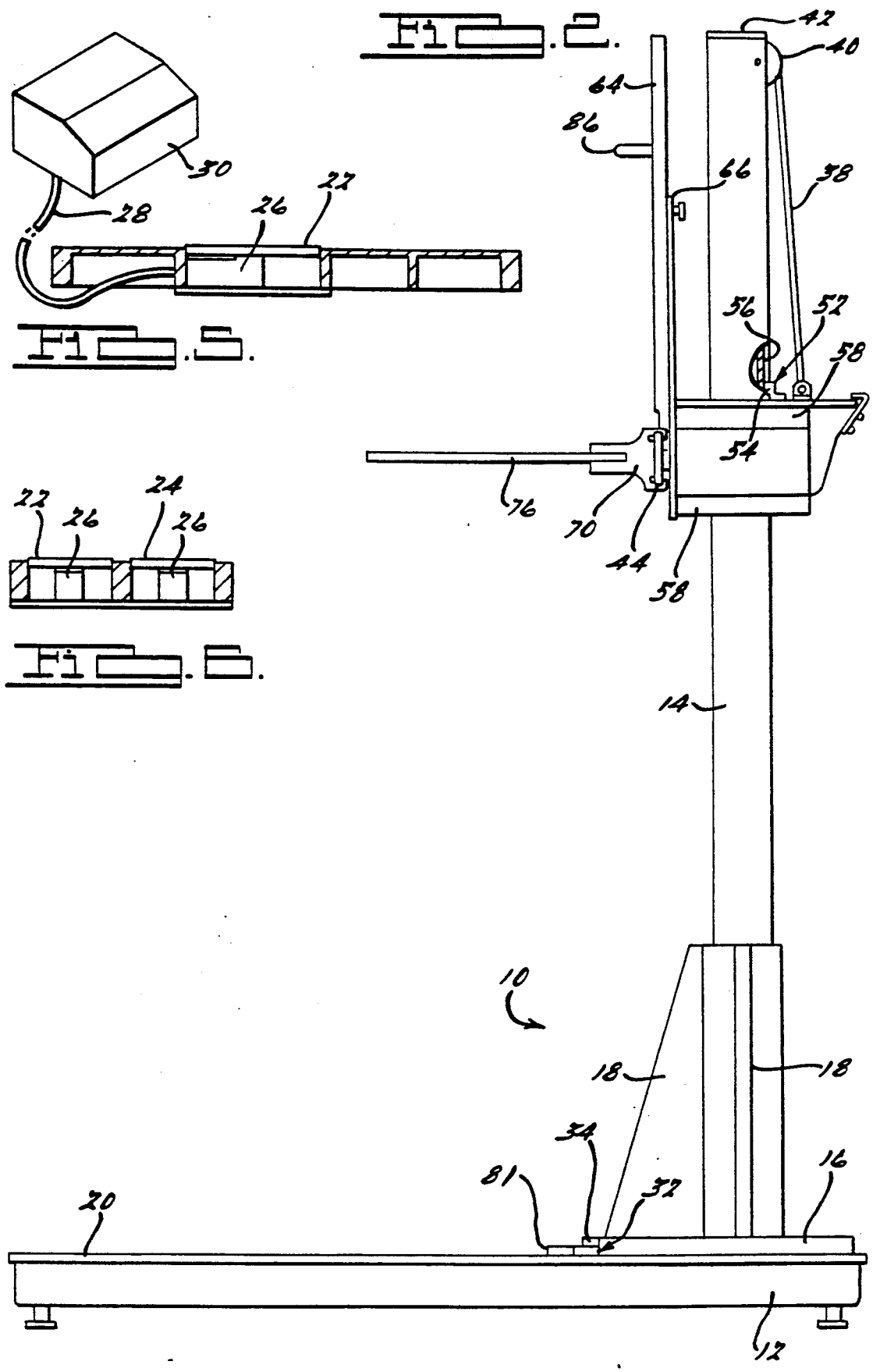
FIG. 2 is a side elevational view of the machine illustrated in FIG. 1.
Figure 3:
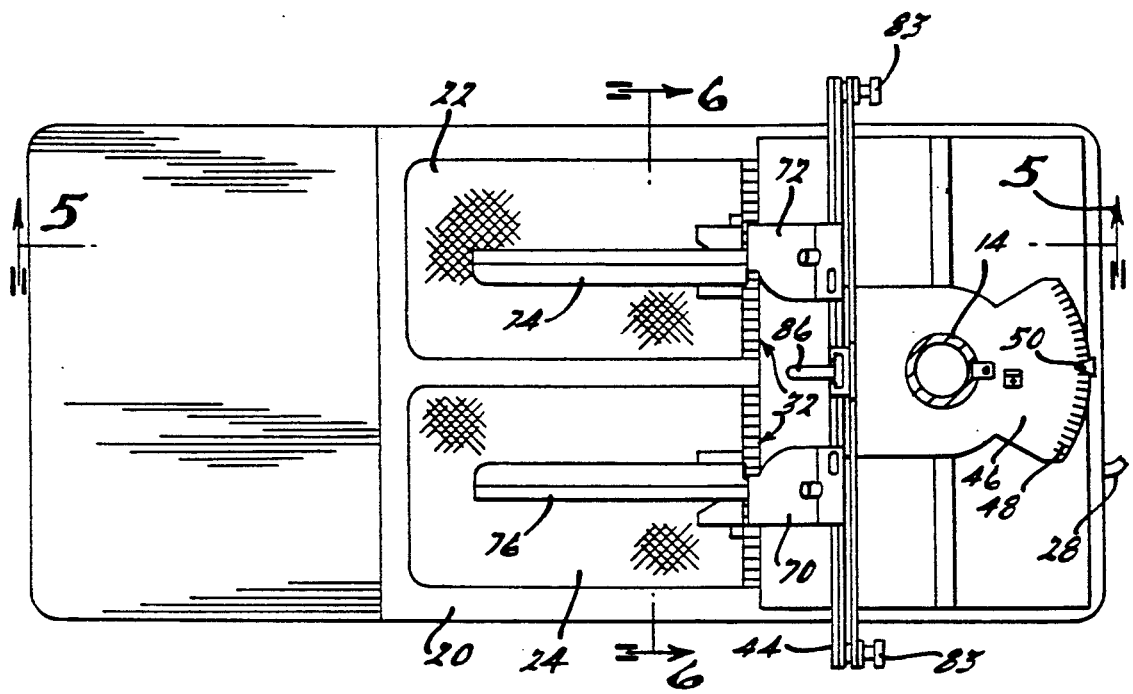
FIG. 3 is a plan view of the machine illustrated in FIG. 1.
Figure 4:
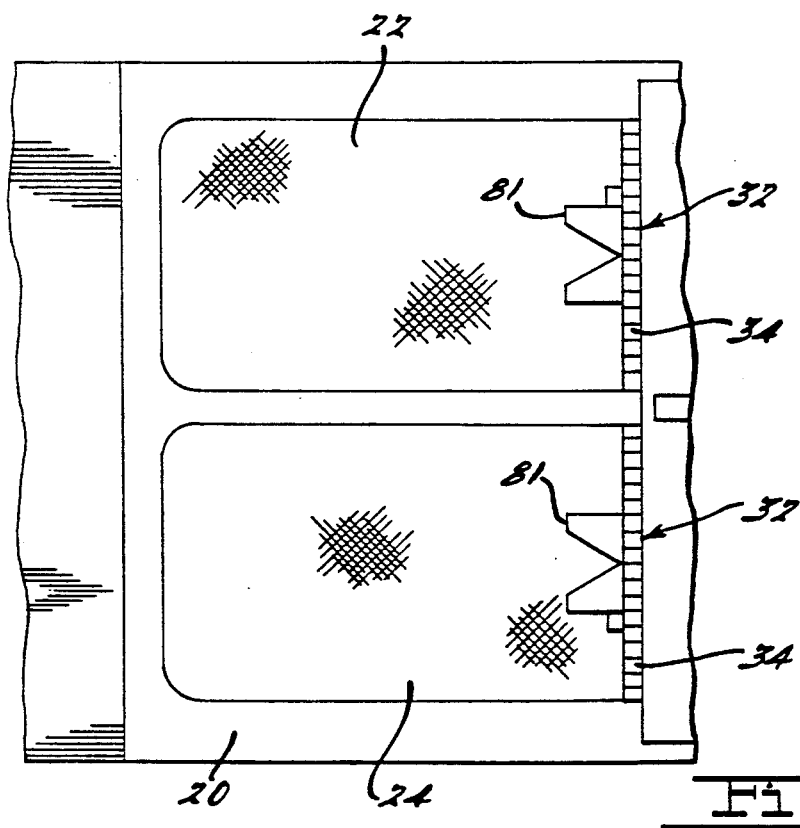
FIG. 4 is a plan view of a portion of the machine illustrated in FIG. 1.

Referring now to the figures, the machine 10 has a base 12 from which a vertically extending column 14 is supported and reinforced by a plate 16 and webs 18. A top plate 20 is secured to the top of the base 12 and includes platforms 22 and 24 for receiving the feet of a patient and for measuring gravitational stress in a patient's body.

Transducers 26 are located underneath each of the platforms 22 and 24 for converting the weight measurement sensed by each of the platforms into electrical impulses that are sent over a line 28 to indicator 30 where the impulses are read and displayed as a digital weight readout. After skeletal adjustments new readings may be taken on machine 10 to see if the weight imbalance and other skeletal postural-distortions have been corrected. Locating means 32 are mounted on the platforms 22 and 24 for lateral movement thereon toward and away from each other in the horizontal plane. Locating means 32 comprise heel-positioning flanges 34 at the rear thereof for locating the body of a patient relative to the machine.

A hollow cylindrical sleeve 36 slides up and down on the column 14 and is rotatable thereabout. The sleeve is counterbalanced by a cable 38 which extends over a counterbalancing wheel 40 and secured to a weight (not illustrated) within the column. The wheel 40 is mounted on an angularly movable cap 42 located in the top of the column 14. A transversely disposed fixed plate 44 is secured to the sleeve 36 and is movable vertically and angularly therewith. A vertically movable transverse plane indicating plate 46 has a scale 48 thereon by which the amount of angular movement may be indicated by a finger 50 secured to the rotatable sleeve 36. The indicating plate 46 has an angle element 52 secured thereto with the upstanding end 54 disposed within a vertical slot 56 in the column 14 which prevents the plate 46 from turning. The cylindrical sleeve 36 is supported between spaced rings 58 of the plate 46 for angular movement about the column 14. The finger 50 secured to sleeve 36 indicates the amount of angular movement of the sleeve and plate 46 as indicated on the scale 48. The fixed plate 44 has a cross bar 60 secured thereto by a pivot 62 midway between the ends thereof. The pivot 62 also secures a vertebral probe slide bar 64 thereon forwardly of an upward extending vertebral indicator 66 which has a scale 68 thereon.

Right and left-handed housings 70 and 72 are mounted on the cross bar 60 for movement toward and away from each other and also angularly in the horizontal plane. The housings 70 and 72 have pivoted pelvic arms 74 and 76 which are mounted thereon for angular movement, in a horizontal plane to extend in parallel relation, as illustrated in the Figures, or at 45 degrees or 90 degrees therefrom in which positions they an be locked by the pelvic arm lock levers 78 which are moved angularly toward the rear when in locked position. The arms 74 and 76 are movable toward and away from each other and upwardly and downwardly with the sleeve 36 to reach a position where they rest upon the ilii of a patient giving a space reading on the scale 80 on the top of the cross bar 60. From the scale readings, the locating means 32 on each of the platforms 22 and 24 are adjusted toward or away from each other to insure that the weight of the body is carried on points immediately below the uppermost point of each ilium. This will also require the feet of the patient to be separated a distance which conforms to the spacing of the ilii.

A pelvic scale 82 is located on the left side of the fixed plate 44. A finger 84 on the end of the pivoted bar 60 to indicate offset of the ilii. The locating means 32 comprises heel plates 81 at one end of the platforms 22 and 24. Heel plates 81 are movable in horizontal plane relative to the heel-positioning flange 34. Heel plates 81 have means (not shown) for fixing their position relative to the heel-positioning flange 34. When the means for fixing their position is released, heel plates 81 are permitted to move a short distance toward and away from each other. Such movement positions the feet of the patient standing on the platform a predetermined distance apart as determined by a scale on the flange 34 conforming to the reading obtained for the spacing of the ilii by the arms 74 and 76. After the cross bar 60 and the slide bar 64 have been angularly adjusted, they may be secured in position by the thumb screws 83. When a measurement is made, the cross bar 60 may be tilted in the vertical plane so that a reading on the end pelvic scales 82 may be obtained from the finger 84 on the ends of the pivoted bar 60 to show the offset of the ilii in the vertical plane. Also, a rotational distortion is usually found which may be read on the scale 48 of the plate 46. The height of the ilii ma be read from the vertical scale (not shown) located within a slot (not shown) in the back of the column 14.

The vertebral probe slide bar 64 has a vertebral probe 86 disposed therein for vertical movement in the slide recess 88. The bar 64 is secured on the pivot 62 and can move angularly to have the probe 86 follow the position of the vertebrae as it is moved upwardly and downwardly in the slide recess 88 of the bar 64.

When the indicator 30 provides an indication that a weight imbalance is present, other indicators of the machine, such as the relative height of the ilii, are interpreted to determine if a contractured leg is present. Approximate treatment can then be determined such as skeletal adjustments, shoe lifts, etc.

In more detail, the process of this invention involves the determination of data about the atlas vertebra and the immediately subjacent vertebrae in the cervical spine, i.e., the first seven vertebrae designated C-1–C-7, inclusive, and recording the position thus determined for, particularly the atlas vertebra, in each of the three planes of possible movement. These three planes are the frontal, sagittal and transverse planes. This determination is accomplished by using X-rays with proper alignment and adjustments to insure accuracy of interpretation of X-rays in each of the three planes to enable the degrees of inclination to be accurately observed and recorded. Such X-rays provide the exact location of atlas vertebra in each of the lateral, sagittal and transverse planes and determine its positional relationship to the occiput and to subjacent vertebral segments. Additional information as to the location of the dorsal vertebrae, particularly the location of the first and second vertebra at the upper end of the chest cavity and including the first thoracic vertebrae are determined for any deviation from the vertical axis, that is, the vertical line of intersection of the frontal and sagittal planes which bisect the human body at right angles. The frontal plane is the plane which bisects the body of a human in the standing position that includes both of the shoulder bones and each ilium. The sagittal plane bisects the spine and the skull at right angels to the frontal plane.

A determination of the distortions in the lumbosacral area is made by determining deviations which may exist from the axes of the frontal and sagittal planes of the pelvic girdle. Specifically, a measurement is made of such deviations by positioning a human in a standing position on separate support surfaces for each foot and while the human is standing in an erect position, as nearly vertical as possible, the distance between the uppermost portion of each ilium is measured. For the purpose of determining an accurate deviation of the uppermost portion of each ilium from the axes of the frontal and sagittal planes, and for obtaining an accurate determination of weight distribution, it is important to insure that the spacing of the feet is such that the weight of the body is carried on points immediately below the uppermost point of each ilium. An adjustment to insure such a condition is made by carefully positioning the center portion of each heel bone at a spacing such that the width between the heel bones is identical to the width between the uppermost portion of each ilium. Measurements are then made to determine whether the uppermost portion of each ilium lies in a single horizontal plane, or deviates there-from. Measurements of the distribution of weight are also taken. A separate determination is made as to whether the uppermost part of each ilium lies in a frontal plane which is at right angles to the sagittal plane and any deviation therefrom is recorded. Such deviation actually constitutes a rotation of the plane of the upper part of each ilium.

When the above measurements have been made, and an adjustment is made to the atlas vertebrae, a post measurement is taken to determine whether a distortion of the pelvis still exists. This determination is made by positioning each foot on the supports, determining the location of the uppermost part of each ilium relative to the vertical axis, i.e., the axes of the frontal and sagittal planes, and making a comparison between the locations so determined and the locations determined prior to the adjustment of the atlas vertebrae.

The process of this invention is useful for checking the degree of correction of spastic contracture resulting from an atlas adjustment shortly after the adjustment is made; in a similar manner, it is particularly useful in checking for pelvic distortion with the passage of time after an adjustment, without repeat X-rays.

The machine 10 and process of the present invention is unique in determining the absence or the degree of the presence of interference with nervous conduction at the spinal level of the top cervical vertebrae (C-1) as expressed in terms of weight distribution and bodily distortions. It determines whether an adjustment thereof is required. It measures the effectiveness of such adjustment immediately following such adjustment and the degree to which it is corrective and, on succeeding checks, the length of time the correction remains stabilized. The machine also measures the state and degree of muscular and/or skeletal stress of the body. It measures the degree of pelvic-girdle distortion into the frontal, sagittal and the transverse planes (orientation) of motion so that relationships to the misalignments of C-1 into the frontal, sagittal and transverse planes can be established and compared. The machine indicates the influence of fatigue, stress, and other debilitating factors on the body in terms of bodily distortions. It predicts the onset of a C-1 subluxation and indicates changes in the misalignments of a C-1 subluxation indicative of the need for correction vector changes in the adjustment and a reevaluation of the subluxation listing.

The machine 10 reduces the need for unnecessary X-ray exposure by providing a means by which to determine if a trauma suffered by the patient since the original X-rays were taken was sufficient to change the original subluxation listing. The machine can measure changes in the weight distribution and in the height of the crests of the pelvis before and after an adjustment of C-1, and record deviations of individual vertebral segments in relation to the pelvic-girdle, as well as the effects of a C-1 adjustment on such deviations. The machine provides a measurable means of establishing the patients' progress in terms of weight distribution, bodily distortion, positive evidence of improvements, no improvement, or regression. The machine provides a data retrieval system, based on measurement, for comparing the patient's symptoms with body stress and can indicate whether a C-1 subluxation has been reduced to 0 degrees in all planes.

It will be appreciated that the recorded deviations of weight distribution and of the pelvic girdle region, as above described, can be readily repeated at any time it is desired to recheck the relative location of the vertebrae which may have been previously determined and recorded by merely following the above described steps in the same order and under the same conditions as expressed. The present invention thus provides an easy, fast, inexpensive but reliable machine and procedure for accurately determining the patient's relative weight distribution, and also for determining the location of key vertebrae in humans. These measurements may be repeated without the necessity for additional X-ray photographs of the various planes of possible motion of the atlas vertebrae.

It should be recognized that while the above description constitutes the preferred embodiments of the present invention, the invention is susceptible to modification, variation, and change without departing from the proper scope and fair meaning of the accompanying claims.

What is claimed is:

1. In an improved checking machine for determining a patient's skeletal misalignments and postural distortions including a base, a top plate for said base, a column extending upwardly from said top plate near one end of the base, a cylindrical sleeve on said column for moving upwardly and downwardly and angularly thereon, a fixed transverse plate on said sleeve for rotation and vertical movement therewith, a cross bar pivotedly secured to said plate forwardly thereof, a pair of slidable housings movable toward and away from each other on said cross bar, and arms secured to said housings and movable angularly from a horizontal plane to indicate tilt and movable laterally of each other to increase or decrease the distance therebetween, the improvement comprising:
   a pair of platforms mounted at equal fixed heights above the top plate for receiving the feet of said patient;
   means for indicating the amount of the patient's body weight resting on each platform; and
   means for adjusting the relative position of the patient's feet to insure that said feet are directly below said patient's ilii.

2. A checking machine as recited in claim 1, wherein the weight indicating means comprises transducer means that converts the deflection of each said platforms due to a gravitational weight imparted by the patient's foot to electrical signals that are displayed as a digital weight readout on an indicator.

3. A checking machine as recited in claim 1, wherein a heel locating means is provided for positioning the patient's foot in desired horizontal positions on said platforms.

4. A checking machine as recited in claim 3, wherein said heal locating means includes right and left plates for engaging with the patient's heels and a scale.

5. A checking machine as recited in claim 3, further comprising:
   a vertically disposed slide bar having its bottom end pivoted to the fixed transverse plate;
   a probe extending rom the slide bar for vertical movement therealong; and a scale on an extension of the fixed transverse plate by which the angular position of the probe is obtained.

6. A checking machine as recited in claim 1, wherein a scale on the end of the fixed plate indicates the amount of tilt of the arms, housing and cross bar, and a scale on said sleeve indicates the degree of rotation thereof and of the plate which is fixed thereto about the column.

7. A checking machine as recited in claim 1, wherein a vertical scale is provided along the column, and means on said cylindrical sleeve for indicating a point of elevation on the column scale.

8. A machine for checking skeletal and postural distortion comprising:
 a base;
 a top plate for said base;
 a pair of platforms fixedly mounted at the same height above the top plate for receiving the feet of a patient;
 means attached to said base for measuring the relative position of each ilium of the patient with respect to said patient's feet attached to such base; and
 means for measuring the amount of the patient's body weight resting one each platform separately, whereby skeletal distortions can be determined.

9. The machine of claim 8, wherein said means for measuring the relative position of each ilium comprises:
 a pair of arms extending horizontally above said base, for engaging with the top of each ilium of the patient;
 means for measuring the relative height of each arm; and
 means for measuring the width of each arm.

10. The machine of claim 9, further comprising means for adjusting the horizontal position of the feet of the patient and said platform whereby the location of the patient's feet can be adjusted to be directly below the patient's ilii.

11. The machine of claim 8, wherein said weight measuring means further comprises an electrical transducer and a digital display unit for displaying the weight on each platform.

12. A process for determining the need for adjustment to be made to the vertebrae in the human spine which comprises the steps of:
 a) establishing the location, by X-ray, of the atlas vertebra in each of the frontal, sagittal and transverse planes;
 b) positioning a human in a standing position on separate fixed height support surfaces for each foot;
 c) determining the width of the uppermost part of each of said human's ilii and adjusting the spacing between the feet such that the width between the center of each heel is the same as the width between each said uppermost part of each ilium, and also so that the patient's feet are directly below the ilii;
 d) determining the weight of the patient on each support surface separately; and
 e) determining the deviation of the uppermost portion of each ilium from the axis of the lateral and sagittal planes.

13. A process for determining the effectiveness of an adjustment made to the vertebrae in the human spine which comprises the steps of:
 a) positioning a human in a standing position on separate fixed height support surfaces for each foot;
 b) determining the width of the uppermost part of each of said human's ilii and adjusting the spacing between the feet such that the width between the center of each heel is the same as the width between said uppermost part of each ilium, and also so that the patient's feet are directly below the ilii;
 c) determining the weight of the patient on each support surface separately;
 d) determining any deviation of the uppermost portion of each ilium from the axis of the lateral and from the axis of the sagittal plane;
 e) adjusting the location of the atlas vertebra; and
 f) determining any deviation from the axis of the lateral and sagittal plane of each ilium.

14. A method for verifying a previously established location of the atlas vertebrae in each of the frontal, sagittal, and transverse planes, and thereby determining the need for further adjustments to be made to the vertebrae in the human spine, said method comprising the steps of:
 a) positioning a human in a standing position on separate fixed height support surfaces for each foot;
 b) determining the width of the uppermost part of each of said human's ilii and adjusting the spacing between the feet such that the width between the center of each heel is the same as the width between said uppermost part of each ilium, and also so that the patient's feet are directly below the ilii;
 c) determining the wight of the patient on each support surface separately; and
 d) determining the deviation of the uppermost portion of each ilium from the axis of the lateral and sagittal planes.

* * * * *

UNITED STATES PATENT AND TRADEMARK OFFICE
CERTIFICATE OF CORRECTION

PATENT NO. : 5,088,504
DATED : February 18, 1992
INVENTOR(S) : Peter Benesh, et al.

It is certified that error appears in the above-indentified patent and that said Letters Patent is hereby In the Abstract, line 3, "location, of" should read --location of--.

Column 1, line 46, "distoration-stress" should read --distortion-stress--

Column 1, line 63, "patent's" should read --patient's--.

Column 3, line 44, "an" should read --can--.

Column 3, lines 59-60, "A finger 84 on the end of the pivoted bar 60 to indicate offset of the ilii." should read --A finger 84 is located on the end of the pivoted bar 60 to indicate offset of the ilii.--

Column 4, line 13, "ma" should read --may--.

Column 5, line 9, "there-from" should read --therefrom--.

Column 6, line 61, "heal" should read --heel--.

Column 4, line 67, "rom" should read --from--.

Column 7, line 24, "one" should read --on--.

Column 8, line 31, "plane" should read --planes--.

Column 8, line 46, "wight" should read --weight--.

Signed and Sealed this

Ninth Day of November, 1993

Attest:

BRUCE LEHMAN

Attesting Officer

Commissioner of Patents and Trademarks